US00PP11818P2

(12) United States Plant Patent
VandenBerg

(10) Patent No.: US PP11,818 P2
(45) Date of Patent: Mar. 13, 2001

(54) CHRYSANTHEMUM PLANT NAME 'YOBETH'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/224,727

(22) Filed: Jan. 4, 1999

(51) Int. Cl.[7] ..... A01H 5/00
(52) U.S. Cl. ..... Plt./287; Plt./286
(58) Field of Search ..... Plt./287, 286

(56) References Cited

U.S. PATENT DOCUMENTS

P.P. 10,212 * 1/1998 Wain ..... Plt./287

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yobeth', characterized by its uniformly mounded plant habit; decorative-type inflorescences that are about 3.6 cm in diameter; attractive reddish purple-colored ray florets and; numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Yobeth.

The new cultivar is a product of a planned breeding program conducted by the Inventor in Salinas, Calif. The objective of the breeding program is to create new garden-type Chrysanthemum cultivars having inflorescences with desirable inflorescence forms and floret colors and good garden performance.

The new cultivar originated from a cross made by the Inventor in November, 1991, of the *Dendranthema grandiflora* cultivar Bravo (U.S. Plant Pat. No. 6,888) as the female, or seed, parent with an unidentified proprietary seedling selection as the male, or pollen parent.

The cultivar Yobeth was discovered and selected by the Inventor as a flowering plant within the progeny of th estated cross in a controlled environment in Salinas, Calif., in October, 1992. The selection of this plant was based on its desirable inflorescence form and ray floret color.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Yobeth has not been observed under all possible environment conditions. The phenotype may vary somewhat with variations in environment such as temperature, daylength and light intensity, without, however, any variance in genotype.

The following traits have been repeatedly observed and are determined to be the unique characteristics of 'Yobeth'. These characteristics in combination distinguish 'Yobeth' as a new and distinct cultivar:

1. Uniformly mounded plant habit.
2. Relatively small decorative-type inflorescences that are about 3.6 cm in diameter.

3. Attractive reddish purple-colored ray florets.
4. Numerous inflorescences per plant.

The new Chrysanthemum is similar to the parent cultivar Bravo. However in side-by-side comparisons under commercial practice, plants of the new Chrysanthemum differed from plants of the cultivar Bravo in the following characteristics:

1. Plants of the new Chrysanthemum are fuller and more dense than plants of the cultivar Bravo.
2. Plants of the new Chrysanthemum flower about one week later than plants of the cutlivar Bravo grown under natural season conditions.
3. Ray florets of plants of the new Chrysanthemum are reddish purple in color whereas ray florets of plants of the cultivar Bravo are red in color.

BRIEF DESCRIPTION OF THE PHOTOGRAPHS

The accompanying photographs illustrate the overall appearance of the new cultivar. The photograph at the top of the sheet comprises a side perspective view of a typical flowering plant of 'Yobeth'. The photograph at the bottom of the sheet comprises a close-up view of typical inflorescences of the cultivar 'Yobeth'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are mae to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Yobeth.

Commercial classification: Decorative-type garden chrysanthemum.

Parentage:

*Female or seed parent.*—*Dendranthema grandiflora* cultivar Bravo, disclosed in U.S. Plant Pat. No. 6,888.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Stems initially upright, then outwardly spreading giving a uniformly mounded appearance to the plant. Freely branching with lateral branches potentially developing at every node, when pinched, about 10 laterals develop.

*Plant height.*—About 30 cm.

*Plant spread.*—About 43 cm.

*Foliage description.*—Leaf arrangement: Alternate. Length: About 4.7 cm. Width: About 3.5 cm. Apex: Mucronate. Base: Attenuate. Margin: Palmately lobed, sinuses parallel. Texture: Upper and lower surfaces sparsely pubescent. Veins prominent on lower surface. Petiole length: About 1.7 cm. Petiole diameter: About 2 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant, about 10 per lateral stem.

*Flowering response.*—Under natural season conditions, plant flowers in mid to late September in the Northern Hemisphere about 73 days after planting, and flower for at least three weeks depending on weather conditions.

*Inflorescence bud. (Before showing color).*—Height: About 4 mm. Diameter: About 6 mm. Phyllary color: Close to 141A.

*Inflorescence size.*—Diameter: About 3.6 cm. Depth (height): About 1.1 cm. Diameter of disc: About 3 mm.

*Ray florets.*—Shape: Oblong. Length: About 1.6 cm. Width: About 5 mm. Apex: Dentate. Margin: Entire. Texture: Smooth, glabrous, satiny. Orientation: Initially upright, then horizontal. Number of ray florets per inflorescence: Typically more than 100. Color: When opening: Upper surface: 59A, white at base. Lower surface: 59B, white at base. Opened inflorescence: Upper surface: 59B, fading to 59C to 77C to 77D; white at base. Lower surface: 77C to 77D, white at base.

*Disc florets.*—Shape: Tubular, apex dentate. Length: About 3.5 mm. Width: Apex: About 1 mm. Base: About 1 mm. Number of disc florets per inflorescence: Typically about 12. Color: Immature: 154A. Mature: Apex: 9A. Mid-section and base: White.

*Peduncle.*—Aspect: Flexible, angled about 45° to the stem. Length: First peduncle: About 3.4 cm. Fourth peduncle: About 8.5 cm. Diameter: About 1.5 mm. Texture: Pubescent. Color: Close to 147A.

*Reproductive organs.*—Androecium: Present on disc florets only. Anther color: 9A. Pollen: Scare, 9A. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Yobeth', as illustrated and described.

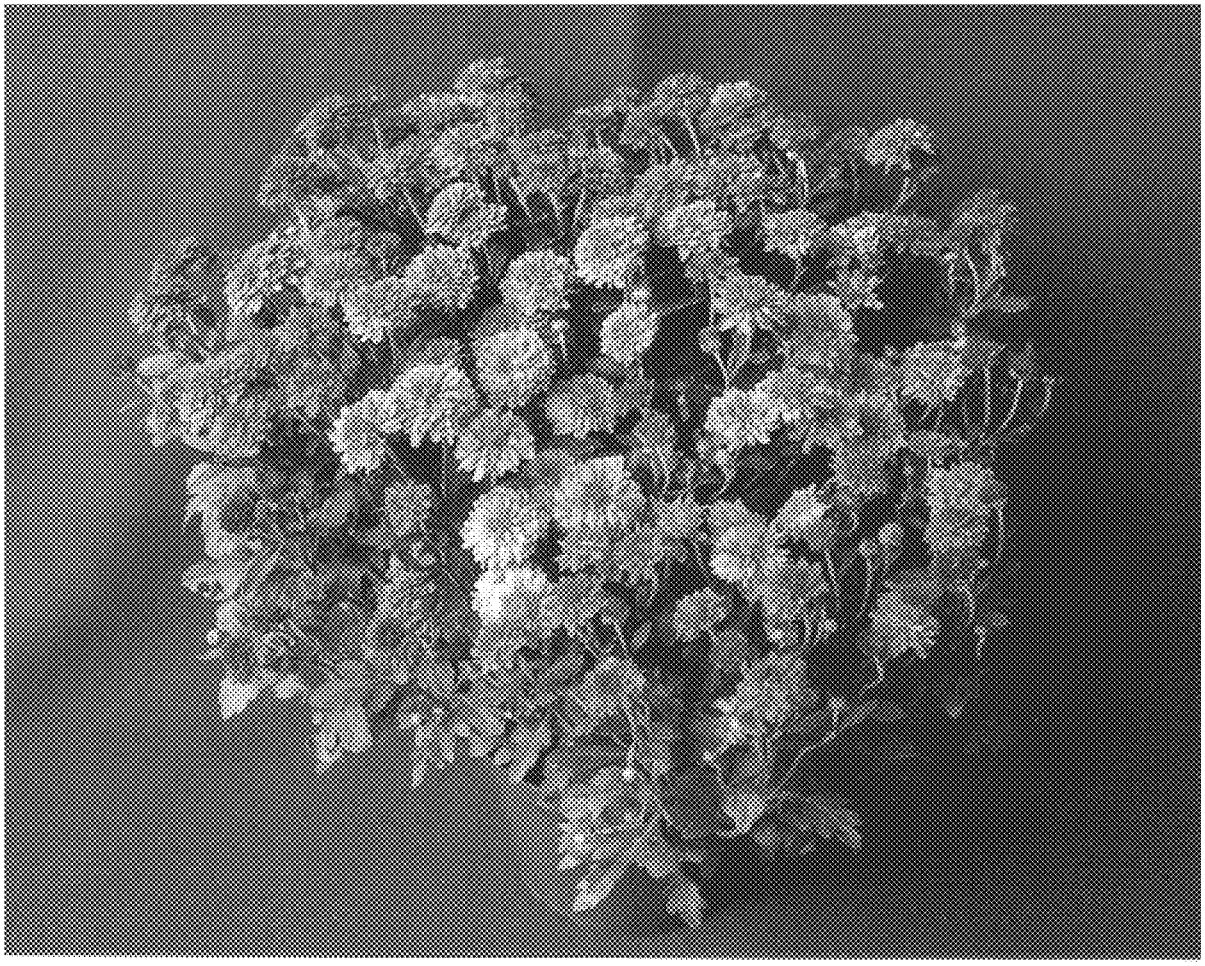
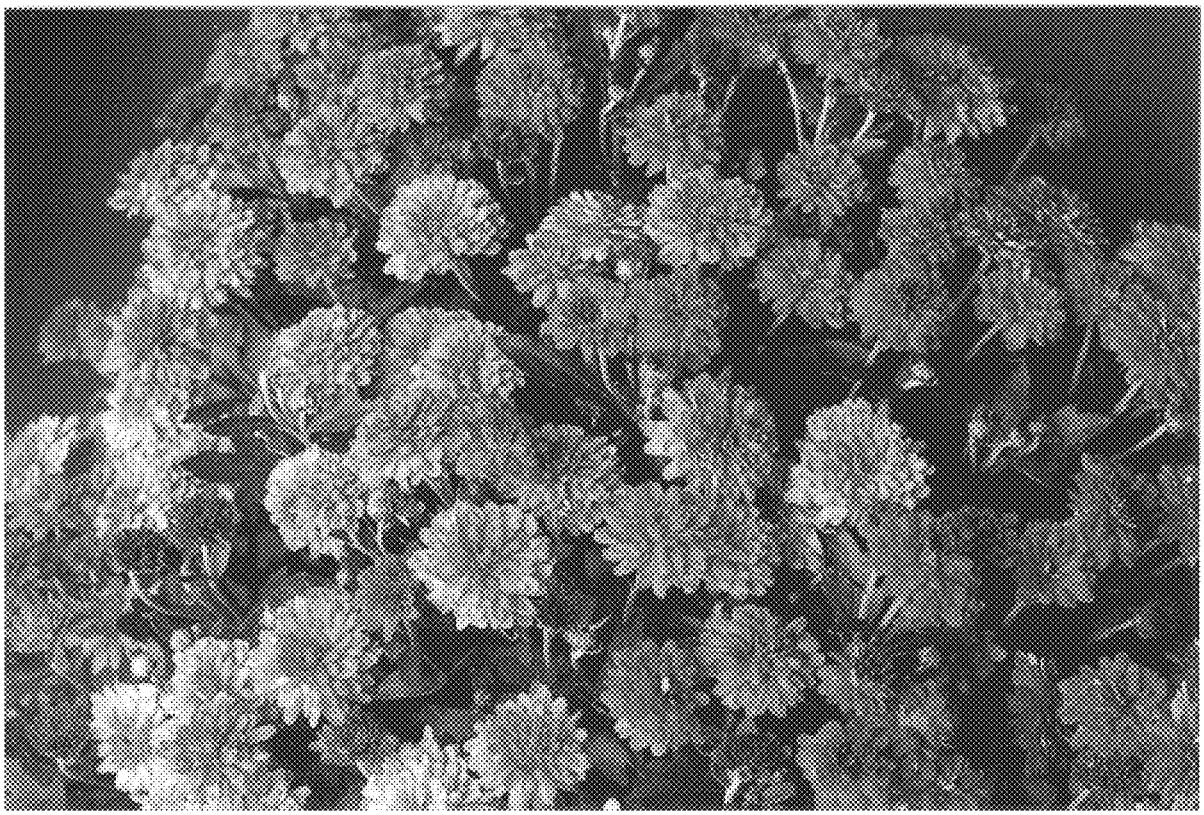

* * * * *